(12) United States Patent
Lew et al.

(10) Patent No.: US 7,179,357 B2
(45) Date of Patent: Feb. 20, 2007

(54) SERIAL SAMPLE INJECTION IN CAPILLARY ELECTROPHORESIS

(75) Inventors: Clarence Lew, Irvine, CA (US); Stephen L. Pentoney, Jr., Chino Hills, CA (US); David L. Yang, Orange, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/280,360

(22) Filed: Oct. 25, 2002

(65) Prior Publication Data

US 2004/0079640 A1 Apr. 29, 2004

(51) Int. Cl.
*G01N 27/26* (2006.01)

(52) U.S. Cl. .................. 204/453; 204/455; 204/605

(58) Field of Classification Search ................ 204/451, 204/453, 601, 604
See application file for complete search history.

(56) References Cited

U.S. PATENT DOCUMENTS

| | | | |
|---|---|---|---|
| 5,169,511 A | 12/1992 | Allington et al. | 204/451 |
| 5,374,527 A | 12/1994 | Grossman | 204/451 |
| 5,543,018 A | 8/1996 | Stevens et al. | 204/461 |
| 5,571,398 A * | 11/1996 | Karger et al. | 204/603 |
| 5,626,732 A | 5/1997 | Allington | 204/453 |
| 5,627,643 A * | 5/1997 | Birnbaum et al. | 356/344 |
| 5,681,751 A | 10/1997 | Begg et al. | 436/89 |
| 5,846,727 A | 12/1998 | Soper et al. | 435/6 |
| 5,935,793 A | 8/1999 | Wong | 435/6 |
| 5,942,443 A | 8/1999 | Parce et al. | 436/514 |
| 5,958,202 A | 9/1999 | Regnier et al. | 204/451 |
| 6,013,166 A | 1/2000 | Heller | 204/469 |
| 6,027,627 A | 2/2000 | Li et al. | 204/603 |
| 6,054,032 A | 4/2000 | Haddad et al. | 204/451 |
| 6,093,296 A | 7/2000 | Soane et al. | 204/451 |
| 6,113,763 A | 9/2000 | Henry et al. | 204/451 |
| 6,143,152 A | 11/2000 | Simpson et al. | 204/451 |
| 6,156,178 A * | 12/2000 | Mansfield et al. | 204/457 |
| 6,207,031 B1 | 3/2001 | Adourian et al. | 204/451 |
| 6,225,061 B1 | 5/2001 | Becker et al. | 435/6 |
| 6,267,858 B1 | 7/2001 | Parce et al. | 204/600 |
| 6,271,038 B1 | 8/2001 | Liu et al. | 204/600 |
| 6,290,831 B1 | 9/2001 | Liran et al. | 204/456 |

OTHER PUBLICATIONS

Peter C. Simpson et al. "Microfrabrication Technology for the Production of Capillary Array Electrophoresis Chips". Biomedica Microdevices. (1998) vol. 1, No. 1. pp. 7-23.*
Q. Fang et al. "Sequential injection sample introduction microfluidic-chip based capillary electrophoresis system." Anal. Chim. Acta. 390, 27-37. (1999).*

* cited by examiner

*Primary Examiner*—Nam Nguyen
*Assistant Examiner*—Jeffrey Barton
(74) *Attorney, Agent, or Firm*—Sheldon Mak Rose & Anderson P.C.

(57) ABSTRACT

The invention is a method of performing electrophoresis that increases sample throughput and increases the efficiency and speed of the analysis of polynucleotides by electrophoresis. The method is performed by loading and running multiple sequential samples on each capillary gel without flushing or replacing the gel between samples.

21 Claims, 4 Drawing Sheets

SERIAL SAMPLE INJECTION IN CAPILLARY ELECTROPHORESIS

BACKGROUND

The automatization of nucleic acid sequencing and separation of polynucleotides from sequencing reaction has enabled the rapid and large scale sequencing of a variety of nucleic acids of interest. Typically, nucleic acid sequencing is performed by incorporating chain terminating nucleotides which are labeled with fluorophores or dyes into the sequencing reaction. The different sized nucleic acid products are separated by gel electrophoresis and detected in automated sequencers. Ongoing large scale nucleic acid sequencing projects require that the nucleic acid sequencing process be as efficient as possible. However, existing nucleic acid sequencing methods are limited by the electrophoresis step.

Current methods fail to maximize the amount of useful data generated from sequenced polynucleotides that are separated and detected by automated electrophoresis. With capillary gel electrophoresis it typically takes between 15 and 40 minutes for the first nucleic acid fragments within a sample to be separated and produce useful data in the form of peaks. This initial time where no useful data is produced is known as "sample dead time", the length of which varies according to the size of the nucleic acid fragments and upon the conditions in which the electrophoresis is performed.

Another factor that limits the rate of useful data produced by current automated capillary gel electrophoresis-based polynucleotide sequencing procedures is that gel is flushed and replaced with a new gel after each sample has been separated and identified by the electrophoresis. This flushing step takes approximately 10 minutes for a complete cycle on a typical automated capillary gel electrophoresis system. Thus, for an electrophoresis run that takes 35 to 150 minutes to perform, useful data is only collected during about 10 to 100 minutes of that electrophoresis run.

What is needed is a electrophoresis method to reduce the sample dead time and increase the efficiency of electrophoresis of nucleic acid samples to enable large scale nucleic acid sequencing projects to be performed more quickly and at an overall lower cost.

SUMMARY

The invention satisfies this need. The invention is a method of performing electrophoresis that increases sample throughput and increases the efficiency and speed of analyzing polynucleotides by improving the duty cycle of automated capillary gel electrophoresis. The method comprises providing a capillary electrophoresis system. The capillary electrophoresis system includes a capillary electrophoresis gel that has a loading end and an elution end. More than one sample is selected. Each sample typically comprises a mixture of different sized polynucleotides, with each size polynucletide having an electrophoretic mobility that corresponds to its size. The smallest polynucleotide in a sample has the fastest electrophoretic mobility and the largest polynucleotide in a sample has the slowest electrophoretic mobility. A first sample is loaded onto the loading end of the gel at time $T_o$, where upon performing electrophoresis the polynucleotide having the fastest electrophoretic mobility in the first sample migrates past a detection window at time $T_F$ and the polynucleotide having the slowest electrophoretic mobility in the first sample migrates past a detection window prior to time $T_S$. Electrophoresis is performed on the first sample. A second sample is loaded onto the loading end of the gel at time $(T_S-T_F)$ and electrophoresis is performed on the second sample such that the polynucleotide with the slowest electrophoretic mobility in the first sample migrates past a detection window in the electrophoretic system before the polynucleotide with the fastest electrophoretic mobility in the second sample migrates past the detection window. A third sample is loaded onto the loading end of the gel at time $2(T_S-T_F)$ and electrophoresis is performed on the third sample such that the polynucleotide with the slowest electrophoretic mobility in the second sample migrates past a detection window in the electrophoretic system before the polynucleotide with the fastest electrophoretic mobility in the third sample migrates past the detection window. The method further includes the steps of sequentially loading additional samples onto the loading end of the gel at time $n(T_S-T_F)$, where n is an integer between 3 and 25. Polynucleotides from each sample are detected as they migrate past the detection window. In one embodiment, the method is performed on more than one sample in more than one capillary gel at the same time.

DRAWINGS

These features, aspects and advantages of the present invention will become better understood with regard to the following description, appended claims and accompanying figures where:

DESCRIPTION

The following discussion describes embodiments of the invention and several variations of these embodiments. This discussion should not be construed, however, as limiting the invention to those particular embodiments. Practitioners skilled in the art will recognize numerous other embodiments as well. In all of the embodiments described herein that are referred to as being preferred or particularly preferred, these embodiments are not essential even though they may be preferred.

The invention is a method of performing electrophoresis that increases sample throughput and allows more samples to be processed within a given time period. The first step of the method is providing an electrophoresis system having an electrophoresis gel. In a preferred embodiment, the electrophoresis gel is a capillary gel. The capillary electrophoresis gel comprises a loading end and an elution end. In exemplary embodiments, the capillary gels have a length of between about 10 cm and about 100 cm in length and the gels comprise a polyacrylamide polymer in an amount of between 1% polyacrylamide polymer and 10% polyacrylamide polymer.

More than one sample is selected. Each sample typically comprises polynucleotides of a different size and having an electrophoretic mobility that corresponds to that polynucleotides size. The smallest polynucleotide in a sample has the fastest electrophoretic mobility and the largest polynucleotide in a sample has the slowest electrophoretic mobility.

The sample containing polynucleotides typically comprises DNA fragments. In a preferred embodiment, the polynucleotides are products of a sequencing reaction. In this embodiment, the polynucleotides of a different size are typically generated by chain terminating nucleotides in the sequencing reaction. The chain terminating nucleotides are labeled with a dye or fluorophore that is specific for each nucleotide. Other polynucleotides, including RNA and modified nucleic acids may be used. Typically, the size of the DNA fragments ranges from between about 20 nucleotides to about 800 nucleotides in length. Alternatively, the samples may comprise other biomolecules, such as proteins, which are to be separated by electrophoresis. An example of sequencing reaction products generated using a PCR amplicon as a template, separated by capillary electrophoresis, is provided in FIG. 1.

Figure 2:
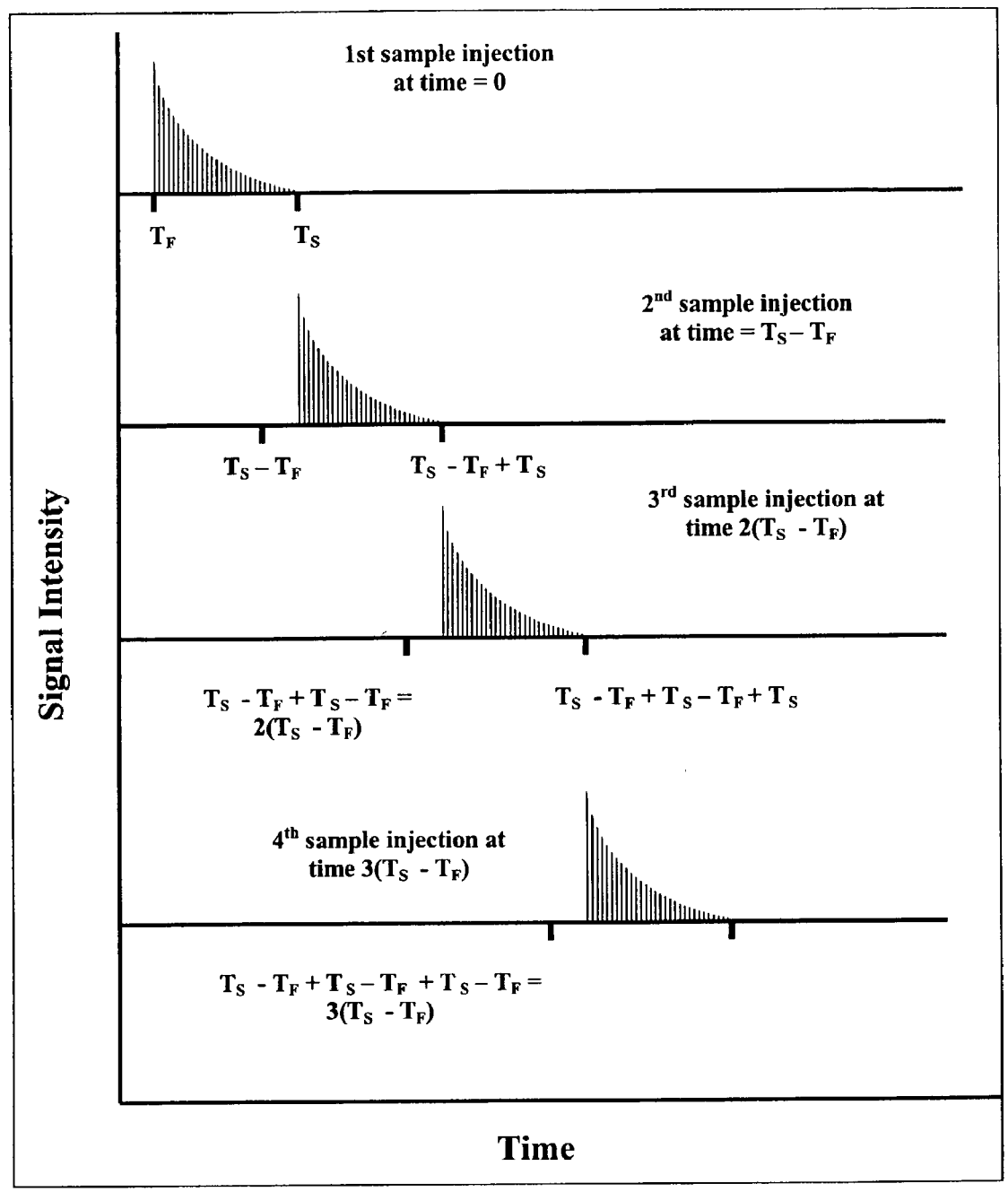
FIG. 2 illustrates an embodiment of the invention for a single electropherogram containing a composite of several sample runs.

The next step of the method is to load a first sample onto the loading end of the gel at time $T_o$. This step may be performed by automated means, for example including that of electrokinetic injection. Electrophoresis is performed on the first sample a predetermined time before loading the second sample onto the loading end of the gel. The injection times for the second and all succeeding samples is typically known in advance or is determined in advance by performing a trial run under set electrophoresis running conditions and by taking into consideration the polynucleotide size variance of a sample. When electrophoresis is performed on the first sample, the polynucleotide having the fastest electrophoretic mobility in the first sample migrates past a detection window at time $T_F$ and the polynucleotide having the slowest electrophoretic mobility in the first sample migrates past a detection window prior to time $T_S$ (FIG. 2).

Electrophoresis is performed on the first sample a predetermined time before loading a second sample onto the loading end of the gel. Polynucleotides from the first sample migrate toward the elution end of the capillary gel, where the polynucleotides are detected by a detector. The step of loading a second sample onto the loading end of the gel is performed at a time such that the polynucleotide with the slowest electrophoretic mobility in the first sample migrates past a detection window in the electrophoretic system before the polynucleotide with the fastest electrophoretic mobility in the second sample migrates past the detection window. Electrophoresis is performed on the second sample such that the polynucleotide with the slowest electrophoretic mobility in the first sample migrates past a detection window in the electrophoretic system before the polynucleotide with the fastest electrophoretic mobility in the second sample migrates past the detection window. In preferred embodiments, the second sample is loaded at time $(T_S-T_F)$, or at a time equivalent to the detection of one peak width after time $(T_S-T_F)$ to prevent the co-migration of the last peak from the first sample and the first peak of the second sample. Thus, the second sample is typically loaded at between $(T_S-T_F)$ and $(T_S-T_F)$ plus the time equivalent to the detection of one peak width. The time equivalent to the detection of one peak width varies according to the sample and electrophoresis run conditions, and as an example can be between 1–30 seconds, and more typically is between 1–10 seconds, and still more typically is between 1–5 seconds. These times may vary according to the sample size and the run conditions. A small amount of variance in the time points $T_o$, $T_F$, $T_S$, etc. is tolerable as long as the overall objective of preventing sample overlap at the detection stage in not compromised.

In preferred embodiments, the method includes the next step of loading a third sample onto the loading end of the gel at time $2(T_S-T_F)$. Electrophoresis is performed on the third sample such that the polynucleotide with the slowest electrophoretic mobility in the second sample migrates past a detection window in the electrophoretic system before the polynucleotide with the fastest electrophoretic mobility in the third sample migrates past the detection window.

In preferred embodiments, the additional steps of the method include sequentially loading additional samples onto the loading end of the gel at time $n(T_S-T_F)$, where n is an integer between 3 and 25 and (n+1) represents the sample number. Typically, n is between 3 and 12.

The final step of the method is detecting polynucleotides from each sample. In a preferred embodiment, the electrophoresis is performed on an automated system such as the Beckman CEQ 2000 DNA Analysis System (Beckman Coulter, Inc., Fullerton). The Beckman CEQ 2000 DNA Analysis System detects the polynucleotides as they pass through the detection window. Polynucleotides from the first sample are detected contemporaneously with the electrophoresis of the second sample. Likewise, polynucleotides from the second sample are detected contemporaneously with the electrophoresis of the third sample.

Thus, the method of the invention eliminates the sample dead time for all but the first sample. This allows multiple samples to be subjected to electrophoresis in a fraction of the time it would otherwise take if each sample were run individually.

In an exemplary embodiment, a total of up to about 25 runs are performed in the same capillary electrophoresis gel without flushing or replacing the capillary gel such that the same capillary polyacrylamide gel is used for the electrophoresis of all samples. More typically, between 12 and 16 samples, or between 8 and 12 samples, are sequentially electrophoresed in the same capillary electrophoresis gel without flushing or replacing the capillary gel.

In a preferred embodiment, electrophoresis is performed on multiple samples in multiple capillary gels at the same time. The method comprising the steps of a) providing a electrophoretic system comprising a capillary electrophoresis gel, the gel having a loading end and a elution end; b) selecting more than one sample, each sample comprising polynucleotides of a different size and having an electrophoretic mobility that corresponds to that polynucleotides size wherein the smallest polynucleotide in a sample has the fastest electrophoretic mobility and the largest polynucleotide in a sample has the slowest electrophoretic mobility; c) loading a first sample onto the loading end of the gel; d) performing electrophoresis on the first sample to separate the polynucleotides; after step d, loading a second sample onto the loading end of the gel at a time such that the polynucleotide with the slowest electrophoretic mobility in the first sample migrates past a detection window in the electrophoretic system before the polynucleotide with the fastest electrophoretic mobility in the second sample migrates past the detection window; and f) performing electrophoresis on the second sample; g) detecting polynucleotides from each sample. In exemplary embodiments, the electrophoretic system comprises between 2 and about 100 capillary electrophoresis gels and electrophoresis is performed on 2 or more capillary gels contemporaneously. However, an electrophoretic system comprising more than 100 capillary electrophoresis gels is within the scope of the invention.

The method of the invention can be seen to provide an electrophoresis method capable of reducing sample dead time and increasing the speed and efficiency of the electrophoresis process by reducing the duty cycle of automated capillary gel electrophoresis.

Example I

12 Serial Sample Injections for Each Capillary Gel

Electrophoresis was performed on 8 different capillary gels on a Beckman CEQ 2000 DNA Analysis System (Beckman Coulter, Inc., Fullerton). Each capillary gel was loaded serially with 12 samples of DNA fragments produced by a sequencing reaction. The fragments were generated using the Beckman Coulter dye-labeled dideoxy-terminator cycle sequencing kit, part no. 608000, (Beckman Coulter, Inc., Fullerton, Calif.). The template was a 294 base pair PCR amplicon generated from the human papilloma virus.

The separation medium consisted of a high molecular weight polyacrylamide polymer in a buffer consisting of 30 mM TRIS and 100 mM TAPS ([2-Hydroxyl-1,1 bis [hydroxymethyl] ethyl)amino] 1-propanesulfonic acid).

Samples were electrokinetically injected into the 30 cm long gel-filled capillary at 2 kV for 15 seconds while separations were made at 6 kV. A total 96 samples were analyzed on the 8 capillary gels. An electropherogram for one capillary is given in FIG. 3. Within 179 minutes, the 96 samples were resolved and detected on a electropherogram as different colors for each of the four nucleotide resulting in approximately 23,040 called bases {12×8×(294−54)}. The gels were not replaced with fresh gels between samples and the capillary gels were not subjected to realignment between sample runs. A similar analysis using conventional methods would have taken approximately 432 minutes to perform. Accordingly, for this sample the method takes only 42% of the time required for prior art procedures to detect and analyze polynucleotides.

Example II

Projected throughput increase for more than 12 Serial Sample Injections per Gel

Figure 1:
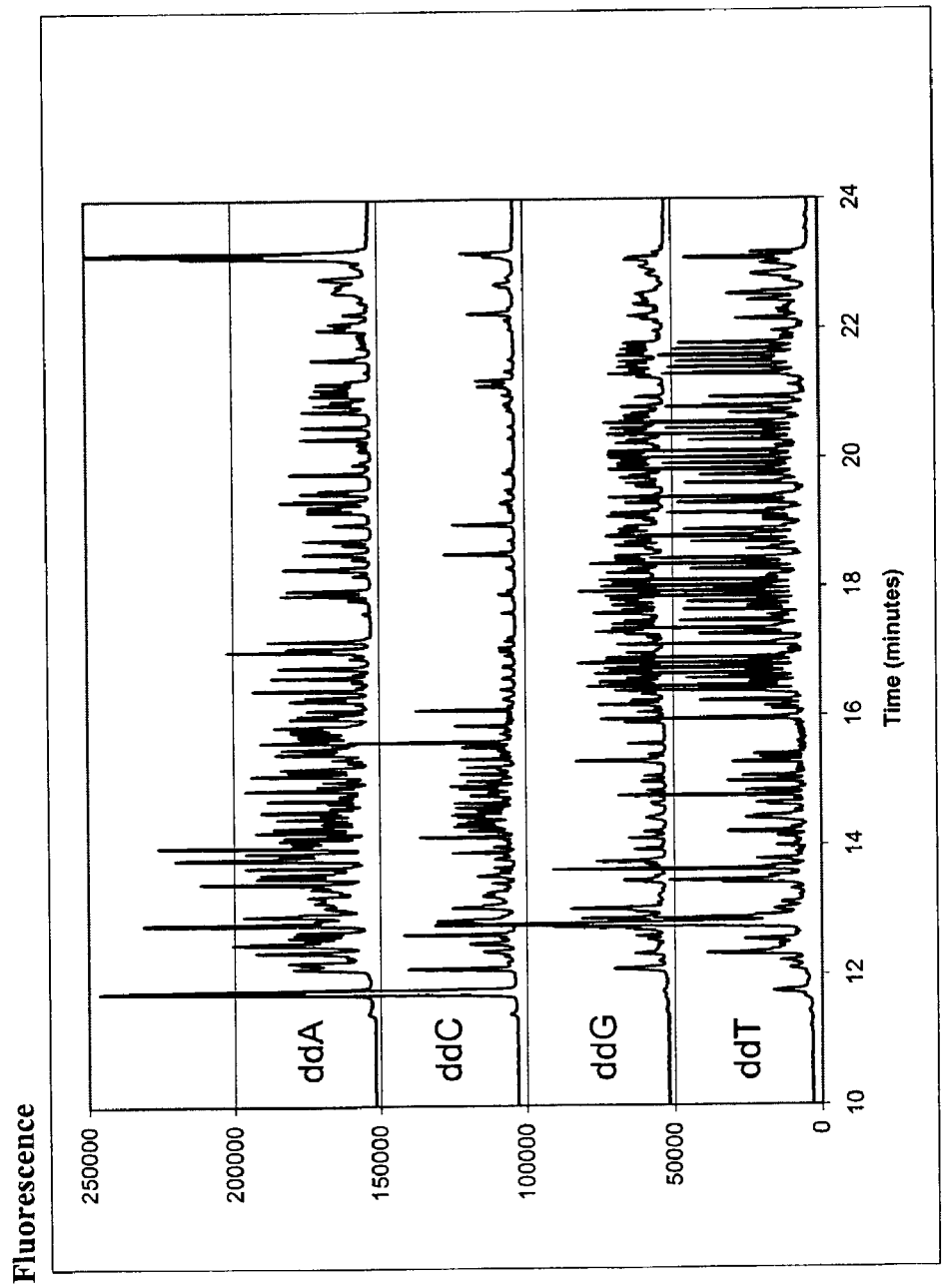
FIG. 1 is a electropherogram for a sequencing reaction run of a PCR product with labeled fragments ranging in size from 54 to 294 bases long.
Figure 3:
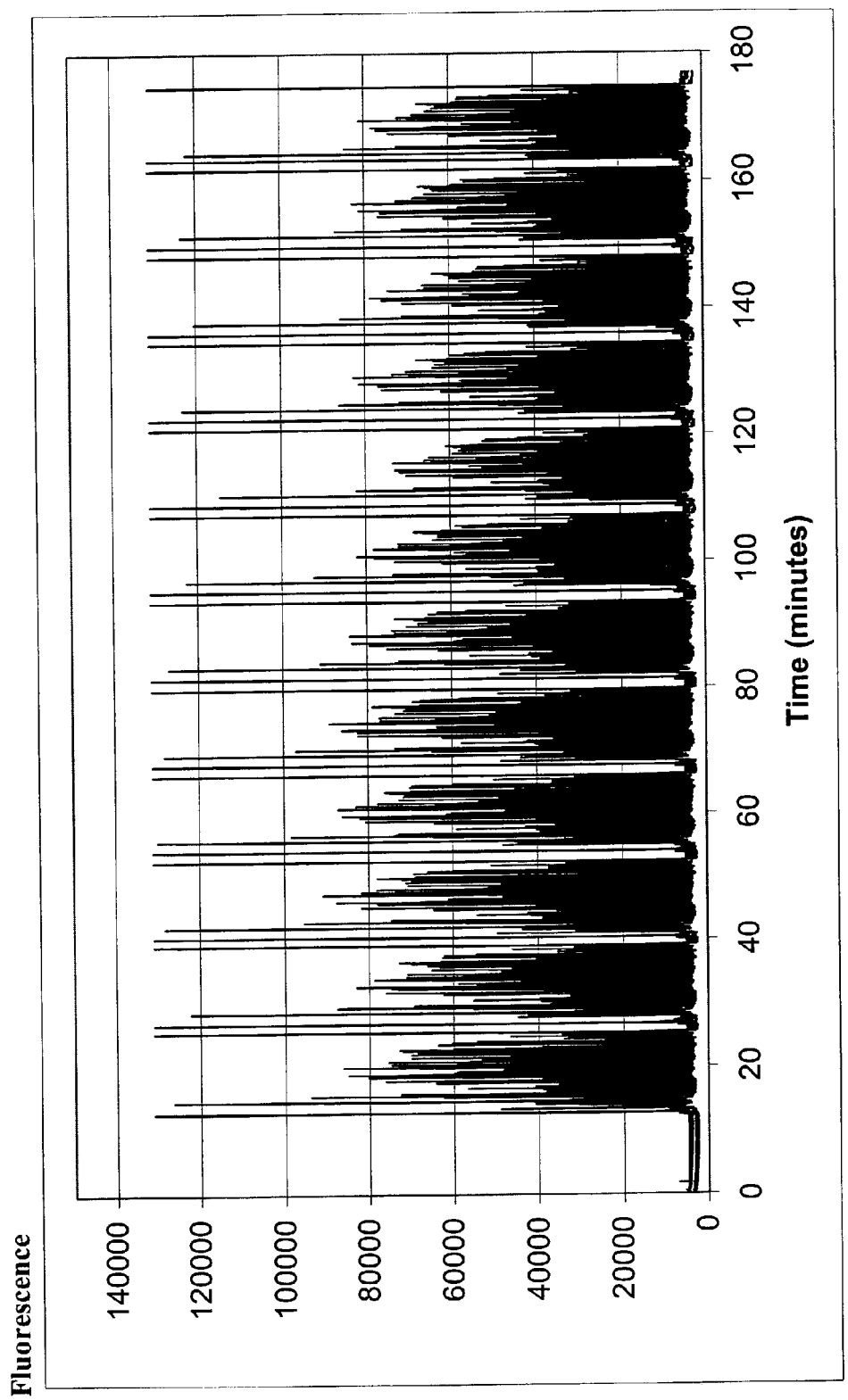
FIG. 3 is a electropherogram resulting from 12 serial injections preformed in one capillary for the PCR product described in FIG. 1.
Figure 4:
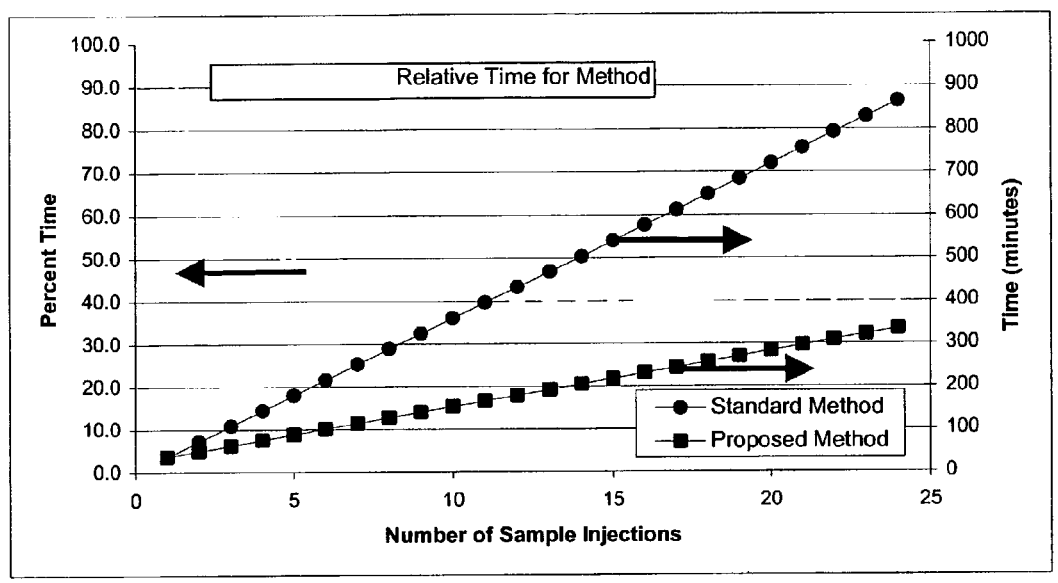
FIG. 4 is a graph illustrating the increased efficiency of the method of the invention over a typical method of the prior art.

FIG. 4 illustrates projected increases in sample throughput for up to 25 serial sample injections per capillary for the example given in FIGS. 1 and 3. The amount of time required for electrophoretic analysis of N samples by conventional methods is 36N, where 36 is the sum of the 10 minute system preparation time, 13 minute dead time, and 13 minute sample time. The total dead time is 23N, which includes the 10 minute system preparation time and the 13 minute dead time per sample. Whereas, with the method of the invention the dead time and sample preparation time approach zero as the number of sample runs increases per capillary and the throughput time is simply 13N. The calculated throughput increase factor (TIF) is 36N/13N=approximately 2.8. Thus, for large numbers of injections, the proposed method will be 2.8×faster than conventional methods. FIG. 2 illustrates the projected times to perform a plurality of sample injections for the method of the invention in comparison to conventional methods.

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. A method of performing electrophoresis, the method comprising the steps of:
   a) providing an electrophoretic system comprising a capillary electrophoresis gel, the gel having a loading end and an elution end;
   b) selecting more than one sample, each sample comprising polynucleotides of different sizes, each polynucleotide having an electrophoretic mobility that corresponds to its size wherein the smallest polynucleotide in a sample has the fastest electrophoretic mobility and the largest polynucleotide in a sample has the slowest electrophoretic mobility;
   c) loading a first sample onto the loading end of the gel at time $T_o$, wherein upon performing electrophoresis the polynucleotide having the fastest electrophoretic mobility in the first sample migrates past a detection window at time $T_F$ and the polynucleotide having the slowest electrophoretic mobility in the first sample migrates past the detection window at time $T_S$;
   d) performing electrophoresis on the first sample;
   e) loading a second sample onto the loading end of the gel at a first predetermined time prior to $T_F$ and performing electrophoresis on the second sample such that the polynucleotide with the slowest electrophoretic mobility in the first sample migrates past a detection window in the electrophoretic system before the polynucleotide with the fastest electrophoretic mobility in the second sample migrates past the detection window;
   f) loading a third sample onto the loading end of the gel at a second predetermined time and performing electrophoresis on the third sample such that the polynucleotide with the slowest electrophoretic mobility in the second sample migrates past a detection window in the electrophoretic system before the polynucleotide with the fastest electrophoretic mobility in the third sample migrates past the detection window;
   g) sequentially loading additional samples onto the loading end of the gel at predetermined times and performing electrophoresis on each sample such that polynucleotide with the slowest electrophoretic mobility from each preceding sample migrates past the detection window before the polynucleotide with the fastest electrophoretic mobility in each succeeding sample migrates past the detection window; and
   h) detecting polynucleotides from each sample as they migrate past the detection window; and
   wherein the third sample or one of the additional samples is loaded after the first sample has migrated past the detection window and before any portion of the second sample has migrated past the detection window.

2. The method according to claim 1, wherein electrophoresis is performed on more than one sample in more than one capillary gel at the same time.

3. The method according to claim 1, wherein each sample contains polynucleotides comprising DNA fragments.

4. The method according to claim 3, wherein the size of the DNA fragments ranges between 20 nucleotides and 800 nucleotides in length.

5. The method according to claim 1, wherein the method is performed on an automated system.

6. The method according to claim 1, wherein a total of between 4 and 16 samples are sequentially electrophoresed in the same capillary electrophoresis gel.

7. The method according to claim 1, wherein a total of between 6 and 12 samples are sequentially electrophoresed in the same capillary electrophoresis gel.

8. The method according to claim 1, wherein the electrophoretic system further comprises between 2 and about 100 capillary electrophoresis gels and electrophoresis is performed on 2 or more capillary gels contemporaneously.

9. A method of performing electrophoresis, the method comprising the steps of:
   a) providing an electrophoretic system comprising a detection window and a capillary electrophoresis gel, the gel having a loading end and an elution end;
   b) selecting more than one sample, each sample comprising polynucleotides of different sizes, each polynucleotide having an electrophoretic mobility that corresponds to its size wherein the smallest polynucleotide in a sample has the fastest electrophoretic mobility and the largest polynucleotide in a sample has the slowest electrophoretic mobility;
   c) loading a first sample onto the loading end of the gel;
   d) performing electrophoresis on the first sample to separate the polynucleotides;
   e) after step d, but prior to migration of the polynucleotide with the fastest electrophoretic mobility in the first sample past the detection window, loading a second sample onto the loading end of the gel at a time such that the polynucleotide with the slowest electrophoretic mobility in the first sample migrates past the detection window before the polynucleotide with the fastest electrophoretic mobility in the second sample migrates past the detection window;
   f) performing electrophoresis on the second sample;
   g) separately and sequentially loading additional samples onto the loading end of the gel and performing electrophoresis on each sample such that polynucleotide with the slowest electrophoretic mobility from each preceding sample migrates past the detection window before the polynucleotide with the fastest electrophoretic mobility in each succeeding sample migrates past the detection window; and
   h) detecting polynucleotides from each sample wherein at least one of the additional samples is loaded after the first sample has migrated past the detection window and before any portion of the second sample has migrated past the detection window.

10. The method according to claim 1, wherein:
   the samples are loaded at a first voltage; and
   electrophoresis is performed on the samples at a second voltage not equal to the first voltage.

11. The method according to claim 9, wherein electrophoresis is performed on the first sample for a predetermined time before loading the second sample.

12. The method according to claim 9, wherein the electrophoretic system further comprises between 2 and about 100 capillary electrophoresis gels and electrophoresis is performed on 2 or more capillary gels contemporaneously.

13. The method according to claim 9, wherein each sample contains polynucleotides comprising DNA fragments.

14. The method according to claim 13, wherein the size of the DNA fragments ranges between 20 nucleotides and 800 nucleotides in length.

15. The method according to claim 9, wherein the method is performed on an automated system.

16. The method according to claim 9, wherein:
   the samples are loaded at a first voltage; and
   electrophoresis is performed on the samples at a second voltage not equal to the first voltage.

17. A method of performing electrophoresis, the method comprising the steps of:
   a) providing an electrophoretic system comprising more than one capillary electrophoresis gel, each gel having a loading end and an elution end;
   b) selecting more than one sample for each capillary electrophoresis gel, each sample comprising polynucleotides of different sizes, each polynucleotide having an electrophoretic mobility that corresponds to that polynucleotides size wherein the smallest polynucleotide in a sample has the fastest electrophoretic mobility and the largest polynucleotide in a sample has the slowest electrophoretic mobility;
   d) loading more than one first sample onto the loading end of the more than one gel at time $T_o$ at a first voltage, wherein upon performing electrophoresis the polynucleotide having the fastest electrophoretic mobility in the first sample migrates past a detection window at time $T_f$ and the polynucleotide having the slowest electrophoretic mobility in the first sample migrates past the detection window at time $T_s$;
   e) performing electrophoresis on the first samples;
   f) loading more than one second sample onto the loading end of the gels at a first predetermined time prior to $T_f$ and performing electrophoresis on the second samples such that the polynucleotide with the slowest electrophoretic mobility in the first samples migrate past a detection window in the electrophoretic system before the polynucleotides with the fastest electrophoretic mobility in the second samples migrate past the detection window;
   g) loading a third sample onto the loading end of the gel at a second predetermined time and performing electrophoresis on the third sample such that the polynucleotides with the slowest electrophoretic mobility in the second sample migrate past a detection window in the electrophoretic system before the polynucleotides with the fastest electrophoretic mobility in the third sample migrate past the detection window;
   h) sequentially loading additional samples onto the loading end of the gels at predetermined times; and
   i) detecting polynucleotides from each sample as they migrate past the detection window;
   wherein the third sample or one of the additional samples is loaded after the first sample has migrated past the detection window and before any portion of the second sample has migrated past the detection window.

18. The method according to claim 17, wherein each sample contains polynucleotides comprising DNA fragments having a size of between 20 nucleotides and 800 nucleotides in length.

19. The method according to claim 17, wherein the method is performed on an automated system.

20. The method according to claim 17, wherein the electrophoretic system comprises between 2 and about 100 capillary electrophoresis gels and electrophoresis is performed on 2 or more capillary gels contemporaneously.

21. The method according to claim 17, wherein:
the samples are loaded at a first voltage; and
electrophoresis is performed on the samples at a second voltage not equal to the first voltage.

* * * * *